United States Patent [19]

Rowe

[11] Patent Number: 4,861,562
[45] Date of Patent: Aug. 29, 1989

[54] FLUIDIZED BED APPARATUS FOR THE MIXING OF FLUIDS AND SOLIDS

[75] Inventor: Frederick Rowe, Middlesbrough, England

[73] Assignee: Imperial Chemical Industries PLC, London, England

[21] Appl. No.: 600,594

[22] Filed: Apr. 16, 1984

Related U.S. Application Data

[60] Continuation of Ser. No. 416,231, Sep. 7, 1982, abandoned, which is a division of Ser. No. 194,931, Oct. 7, 1980, abandoned.

[30] Foreign Application Priority Data

Oct. 18, 1979 [GB] United Kingdom ............ 7936151

[51] Int. Cl.$^4$ .................. B01J 8/38; B01J 8/18; F27B 15/10
[52] U.S. Cl. ............................ 422/143; 34/57 A; 165/104.16; 118/DIG. 5; 201/31; 422/145; 431/7; 432/15; 432/58
[58] Field of Search ............ 422/143, 145, 230; 432/15, 58; 431/7, 130; 34/10, 57 A; 165/1, 104.16; 118/153, 158, 53, 164, 62, 303, 716, DIG. 5; 201/31

[56] References Cited

U.S. PATENT DOCUMENTS

| | | |
|---|---|---|
| 2,378,342 | 6/1945 | Voorhees et al. ............ 422/145 |
| 2,709,625 | 5/1955 | Phinrey ............ 201/31 |
| 2,709,675 | 5/1955 | Phinney ............ 201/31 |
| 2,876,079 | 3/1959 | Upchurch et al. ............ 422/143 |
| 2,935,840 | 5/1960 | Schoppe . | |
| 3,140,862 | 7/1964 | Schoppe ............ 432/58 |
| 3,241,520 | 3/1966 | Wurster et al. ............ 118/DIG. 5 |
| 3,303,017 | 2/1967 | Mayer et al. ............ 422/143 |
| 3,647,357 | 3/1972 | Niedner et al. . | |
| 3,672,577 | 6/1972 | Kramer ............ 422/143 |
| 4,035,152 | 7/1977 | Yang et al. ............ 422/143 |
| 4,117,801 | 10/1978 | Dannelly et al. ............ 118/303 |
| 4,135,885 | 1/1979 | Wormser et al. ............ 422/143 |

FOREIGN PATENT DOCUMENTS 753485 8/1980 U.S.S.R. ............ 118/303

Primary Examiner—Barry S. Richman
Assistant Examiner—Timothy M. McMahon
Attorney, Agent, or Firm—Cushman, Darby & Cushman

[57] ABSTRACT

Process and apparatus for fluidized bed mixing of fluids and gases in which the fluid is injected with a high angular velocity through a relatively narrow, preferably single, orifice (3). The angular velocity may be imparted by injecting the fluid at high velocity tangentially at the periphery of the squate chamber (4) so that angular momentum is gained as it spirals inwards towards orifice (3). Optionally, an open-topped hopper (5) for solids is suspended above orifice (3). The lower end of the hopper (5) terminates in a second orifice (7) located vertically above orifice (3). The solid particles are thereby swept radially outwards towards the wall of the chamber (1) in co-current admixture with the fluid.

4 Claims, 3 Drawing Sheets

FLUIDIZED BED APPARATUS FOR THE MIXING OF FLUIDS AND SOLIDS

This is a continuation of application Ser. No. 416,231 filed Sept. 7, 1982, now abandoned, which was a divisional of application Ser. No. 194,931 filed Oct. 7, 1980, now abandoned.

The present invention relates to a process and apparatus for the rapid mixing of fluids and solids.

In the chemical processing of fluids, particularly gases, and solids it is frequently necessary to obtain rapid and intimate mixing of the solid and fluid components so that uniform and controllable reaction can take place in the process. Examples of processes which require such rapid and intimate mixing include not only those in which reaction between the solid and fluid is the prime objective (as, for example, in the burning of pulverised fuel in air) but also those in which the solid acts primarily as a catalyst (as, for example, in catalytic cracking of hydrocarbons) or as a heat carrier (as, for example, in fluid coking). Materials may be desorbed from the solid surface, (for example in the fluidized-bed drying of grains, foodstuffs and chemicals) or deposited from a gas onto the solid surface (for example in fluid coking or catalytic cracking). Rapid and intimate mixing is of particular importance in processes where product yields are strongly dependent on the reaction parameters of time and temperature. Typical of such processes are those based on a reaction sequence A→B→X where A represents the reactant(s), B is the desired product and X represents unwanted products of overreaction. In an efficient reaction system each molecule of reactant A will be subjected to, as nearly as possible, the same processing cycle, (say heating to reaction temperature, contacting with catalyst, disengagement from catalyst and quenching (cooling)), as all the other molecules of A. On optimisation of the processing cycle the yield of B will be maximised. If, on the other hand, some molecules of A go through the processing cycle more rapidly than others, or fail to reach the reaction temperature, or to reach the catalyst, then some reactant A will remain unconverted while some will be over-converted to the unwanted products X. In such circumstances, yields of the desired product B will be less than those obtainable by optimisation of an efficient reaction system.

The processing cycle of such a reaction system may be regarded as consisting of three steps, viz:
(a) initiation of reaction;
(b) reaction period; and
(c) quenching.

Clearly, if each molecule of reactant feedstock is to be subjected as nearly as possible to the same processing cycle, each of steps (a), (b) and (c) must provide substantially uniform conditions for all molecules passing through them. However, the provision of such uniform conditions in even one of the three steps should generally lead to increased efficiency of the whole process.

One way in which mixing of fluids, especially gases, with a particulate solid is achieved is by use of a fluidized bed of the solid particles. As is well known, the velocity of the gas passing upwards through the fluidized bed must be maintained within certain limits. If the velocity is too low, the bed will not fluidize. On the other hand, increasing the velocity beyond the optimum point for efficient fluidization increases the rate of "bubbling" of the solid particles and also increases the carry-over of particles from the bed. One problem in maintaining a fluidized bed condition is the production of a uniform stream of fluidizing gas over the area of the bed. Use of a single narrow jet of high velocity gas leads to "spouting" of the bed, excessive carry-over of solids and poor mixing of solids with gas. Many types of distributor have been designed, therefore, to provide uniform spread of the gas as it fluidizes the bed. Such distributors frequently involve the use of several gas inlets spread over the area of the bed.

According to the present invention a process for mixing a particulate solid and a fluid in a fluidized bed of the solid particles comprises injecting the fluid into the bed of particles through an orifice which is relatively narrow in comparison with the overall width of the bed, the injected gas stream having imposed upon it an angular velocity which is high in comparison with its linear velocity of injection into the bed.

Preferably, the fluid is a gas and more preferably a single stream of gas is injected into the bed through a single orifice. The use of an injected fluid of high angular velocity enables rapid mixing of the solid particles and injected fluid to occur, the solid particles being drawn into the vortex created by the high angular velocity of the jet of fluid. Preferably, the diameter of the orifice through which the fluid is injected is less than 1/5, more preferably less than 1/10 of the overall width of the bed.

Better control of the mixing is achieved in a preferred embodiment of the process of the invention in which the injected stream of fluid, preferably gas, is mixed with a stream of solid particles issuing from a second orifice located substantially vertically above the orifice through which the fluid stream is first injected into the bed. In this preferred embodiment, the combination of an inlet stream of high angular velocity and the use of two vertically aligned orifices, one for the inlet stream and the other for solid particles allows the high angular momentum of the incoming fluid to be used in accelerating the solid particles radially outwards in co-current admixture with the fluid, thus ensuring extremely rapid and uniform mixing of the solid with the fluid. If the inlet stream lacked its high angular velocity, the tendency would be for the solid particles to be blown vertically upwards rather than "swirled" toward the sides of the chamber.

The present invention also comprises apparatus for mixing a solid and a fluid, preferably a gas, comprising fluidized bed apparatus including inlet means for admitting a fluid to fluidize the bed wherein the inlet means comprises an orifice located in support means for supporting the bed of particles, said orifice being narrow in comparison with the overall width of the bed, and said inlet means being adapted to allow a high angular velocity to be imparted to the fluid.

Preferably the orifice diameter is less than 1/5, more preferably less than 1/10, of the overall width of the bed.

In a preferred embodiment of the apparatus of this invention the fluidized bed apparatus includes a second orifice located in a plate member within the apparatus, said second orifice being aligned substantially vertically above the orifice comprising the inlet means for the fluidizing fluid.

As hereinbefore mentioned, presence of the second orifice means that when the apparatus is in use, particulate solid is drawn rapidly down through the second orifice into the vortex created by the rapidly spinning jet of fluid entering through the first orifice. Thus if the second orifice is made the bottom exit of an internal hopper filled by overflow from the fluidized bed of solids there is provided a continuous, dense-phase stream of solids into this vortex, to be mixed very rapidly with the incoming gases or liquids and returned to the fluidized bed. The use of a hopper permits further control over the flow of solid particles to be exercised in that not only the quantity but also the type of particles can be controlled. For example, the temperature and/or composition of the particles issuing from the second orifice can be different from those of the particles already in the fluidised bed.

Embodiments of the process and apparatus of this invention are more particularly described with reference to the accompanying drawings although the invention is not limited to the particular embodiments described and shown.

Figure 1:
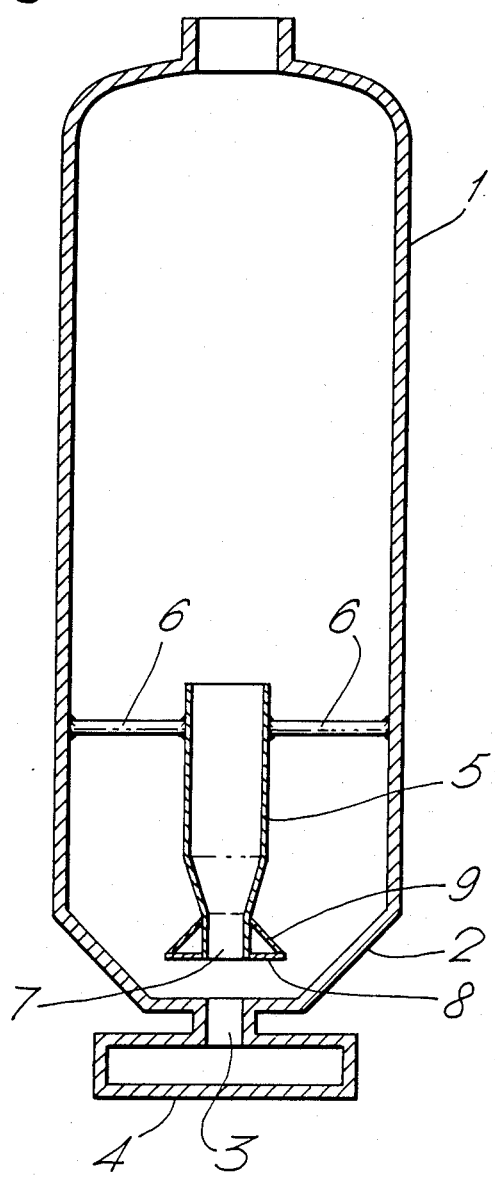
FIG. 1 is a front elevation, partly in section, and of a somewhat schematic nature, of a fluidized bed apparatus according to this invention.

Referring to FIG. 1, the chamber 1 for containing the fluidized bed of solids has a base 2 in which is located a first orifice 3. Connected to the orifice 3 at its lower end is a squat chamber 4. An opentopped hopper 5 is suspended above orifice 3 by supports 6. At its lower end, hopper 5 terminates in a second orifice 7 which is located vertically above the first orifice 3. It is preferred that the second orifice 7 be surrounded by a horizontal flat disc 8 with a diameter at least three times that of orifice 3, with a fairing 9 attached, the fairing serving to prevent accumulation of solids on the dead space on top of the disc.

In use, a bed of suitable particles is contained within the chamber 1. The depth of bed, the dimensions of chamber 1 and hopper 5, and the velocity of the fluidizing fluid are so chosen that the annulus between hopper 5 and the wall of chamber 1 is maintained as a uniformly boiling fluidized bed of solids, sufficiently expanded for an overflow of solids from this annulus back into hopper 5. If desired, the annulus between hopper 5 and the wall of chamber 1 may contain (a) cooling or heating coils to control the temperature of the fluidized bed, and/or (b) baffles to inhibit overall rotary motion of the fluid and solid in the bed. The provision of such coils and/or baffles in fluidized beds will be familiar to those skilled in this art.

The fluidizing fluid is injected through orifice 3 and the fluid stream is given a high angular velocity by any suitable means, for example by injecting it at high velocity tangentially at the periphery of the squat chamber 4 so that the stream gains angular momentum as it spirals inwards towards orifice 3. In this preferred method the relative magnitudes of the angular and linear components of the fluid velocity may be conveniently controlled by varying the geometry of the squat chamber 4 and/or the length of the pipe or conduit connecting the chamber 4 with the orifice 3. For example if the said length of pipe or conduit is too long, the inlet stream may lose much or all of its initial angular velocity so that the solid particles would tend to be blown vertically upwards rather than directed toward the sides of the chamber. On the other hand, if the length of pipe or conduit is too short, a vortex may be set up which drags the solid particles down into the chamber 4. The geometry of chamber 4 and the length of the pipe connecting it to orifice 3 will differ according to the process being carried out in the apparatus but those skilled in this art will be readily able to decide between suitable and unsuitable dimensions for the chamber 4, orifice 3 and the pipe connecting them.

Figure 2:
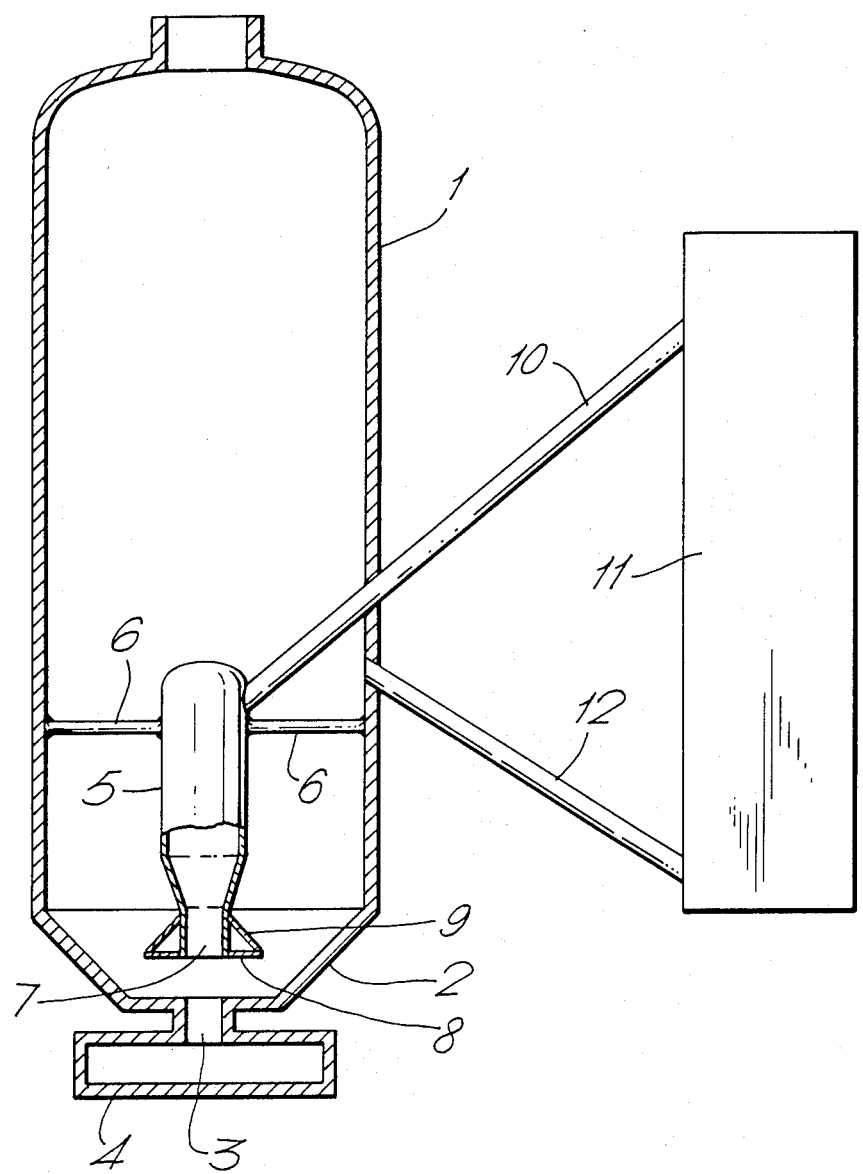
FIG. 2 is a similar view of a modified form of the fluidized bed apparatus shown in FIG. 1.
Figure 3:
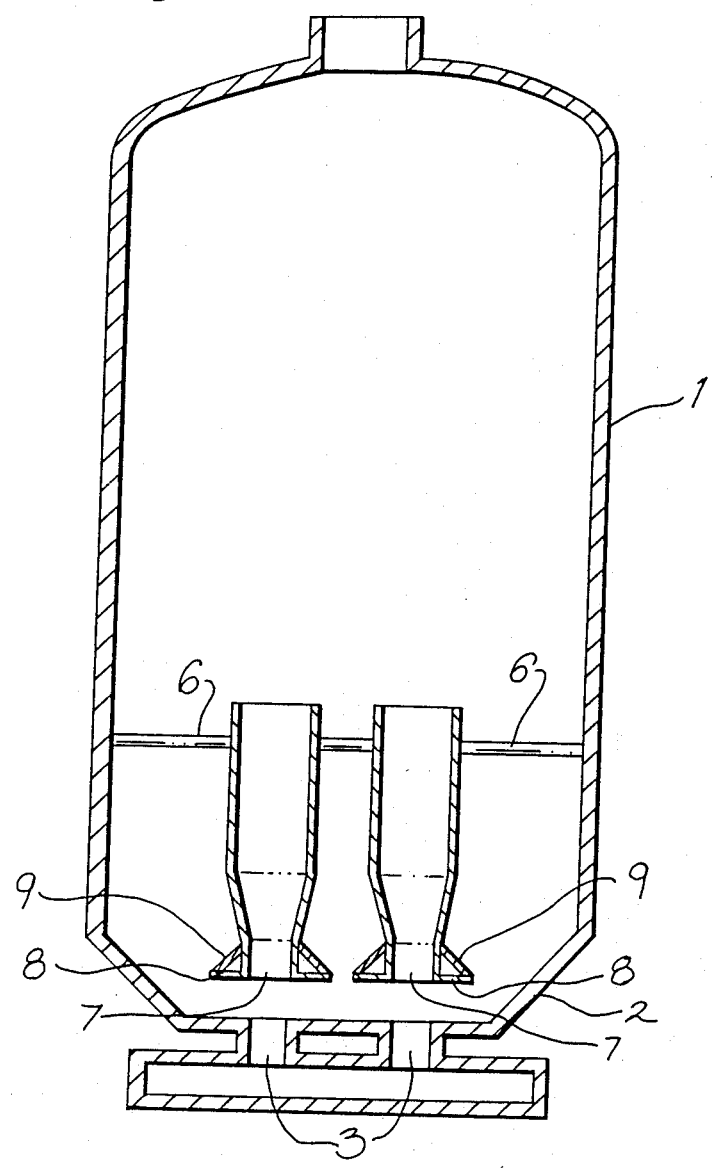
FIG. 3 is a front elevation of an apparatus according to this invention having a plurality of supply conduits.

Referring now to FIG. 2, similar pieces of equipment are allotted the same reference numerals as in FIG. 1 (and FIG. 3). However, hopper 5 has a closed top carrying a feed pipe 10 connected to a separate external treatment unit, represented generally by box 11. Overflow from the fluidized bed flows through pipe 12 into the unit 11. The external treatment unit 11 may be used, depending on the process operated in the apparatus, to treat solids entering it in one or more of a number of ways, for example to heat, cool, reactivate, decoke, desulphurise the particles. The purpose of unit 11 is to treat the particles so that on their return to hopper 5 they have the desired properties for the particular reaction being carried out in the fluidized bed.

One example of the process of this invention using the apparatus shown in FIG. 1 is a process in which the heat required to carry out an endothermic reaction is provided by admixing preheated solids with a relatively cool gaseous or vaporised feedstock, for example a fluid coking process. In this process, the vaporized feedstock is injected through orifice 3 and the hot solids from hopper 5 are drawn into the vortex above orifice 3 through orifice 7. In this process it is necessary to maintain the temperature of the solid particles significantly above that of the feedstock. This is achieved either by immersing heating coils in the fluidized bed or by injecting hot, inert, gases into the bed through separate injection points additional to orifice 3 or preferably by means of the apparatus shown in FIG. 2. In using the external treatment unit 11 the solid particles are reheated by any convenient means ready for return to hopper 5 via pipe 10. Thus, in a fluid coking process, the solid particles entering the unit 11 via pipe 12 have some of the carbon, which has been deposited on them during the coking process, burnt off in a stream of air, thereby raising their temperature prior to their return to the hopper 5. At the same time disc 8 is used to prevent access of other solids from the fluidized bed contacting the incoming gases before the hot solids from hopper 5 are thoroughly mixed with the gases. In this way the gases are subjected to a very uniform, rapid rate of heating.

A further example of the process of this invention employing the apparatus shown in FIG. 2 is a reaction system in which a gas is contacted with a solid having catalytic properties. It frequently happens in some catalytic processes that after a time the catalyst becomes partially, or even totally, deactivated. A certain amount of deactivation can usually be tolerated but eventually regeneration of the catalyst is usually necessary. Some catalytic processes are carried out in conventional fluidized beds which inevitably contain particles having different degrees of activity. Injection of reactant gas into such beds means that random contact with catalyst particles of widely varying activity is bound to occur. Although steps can be taken to ensure that the residence time in the bed under reaction conditions is uniform for all the feedstock, those molecules of feedstock which contact freshly regenerated catalyst in the bed will be over-converted, while those contacting deactivated particles will be unconverted or at best under-converted.

The process and apparatus of this invention, especially as illustrated in FIG. 2, enable the process operator to alleviate or even overcome the problem of non-uniform conversion of feedstock in a fluidized bed of catalyst particles. In the process and apparatus of the invention contact is made between the gaseous feedstock issuing through orifice 3 and freshly regenerated catalyst particles issuing from hopper 5 through orifice 7. In this embodiment of the invention, the external treatment unit 11 is used to regenerate the catalyst i.e. to restore it to an appropriate degree of catalytic activity as well as to heat it to a temperature appropriate for the catalytic process. Thus, in using the process and apparatus of this invention, the point at which the chemical reaction starts can be sharply defined as the time at which the fluid encounters the solid. At the same time, by using the apparatus shown in FIG. 2, it is possible to contact the fluid with particles of more uniform characteristics than is the case in conventional processes. This embodiment of the invention is of particular value for carrying out reactions in which socalled "regenerable catalyst-reagents" are contacted with a gas stream, for example as described in U.S. Pat. Nos. 4,172,810 and 4,205,194 to Mitchell III et al (Exxon Research and Engineering). Other processes where this embodiment of the invention is of value include those processes where the oxidation state of the catalyst is important, for example in the oxidation of hydrocarbons over oxide catalysts, for example of propylene to acrylic acid and butenes to maleic anhydride, and in the oxychlorination of ethylene or ethane to vinyl chloride. A particular example is the process described in our UK Patent Specification No. 1,373,489 for the conversion of propylene to propylene oxide over a copper catalyst.

A further embodiment of the present invention relates to the rapid quenching of a process gas stream. Rapid quenching i.e. cooling of a process gas stream is important in a number of processes but is especially so in the pyrolysis of hydrocarbon feedstocks for olefines manufacture. Hydrocarbon pyrolysis is carried out at high temperature using short residence times and rapid quenching is necessary in order to inhibit the secondary reactions which are likely to occur under the process conditions. These secondary reactions produce unwanted side products including tars and coke which tend to deposit on the walls of the pyrolysis reactor and associated equipment. Multitubular heat exchangers of elaborate design have achieved some success in quenching pyrolysis products from light hydrocarbon feedstocks, for example ethane and naphtha. Nevertheless, fouling by coke and tars occurs even with these light feedstocks, thereby necessitating expensive interuptions in production for cleaning purposes. With feedstocks heavier than naphtha, indirect quenching of this type suffers from severe fouling and generally a combination of direct quench, for example with water or heavy oil, and elaborate heat exchangers is used. A further disadvantage is that use of such a combination lowers the efficiency of heat recovery from the reaction, since the heat is inevitably recovered at a relatively low temperature.

The process and apparatus of this invention, for example as described and illustrated with reference to either FIGS. 1 or 2, may be used to alleviate this quenching problem. In relatively mild cases, where tar and coke by-products are a relatively small proportion of the total products, it is convenient to use the apparatus of the invention, for example as illustrated in FIG. 1, with the addition of cooling coils immersed in the fluidised bed in the annulus between the hopper 5 and the inner wall of chamber 1. Preferably, in such a case, the temperature of the fluidised bed is maintained at around 400° C. and heat is recovered as high pressure steam raised in the cooling coils. At this order of temperature, secondary reactions are acceptably slow. Optionally, the disc surrounding the second orifice (disc 8 in FIG. 1) may be omitted in this embodiment of the invention although its presence may be desirable in some circumstances in order to establish the optimum flow pattern within the fluidized bed reactor.

Preferably the quantity and size distribution of particles in the fluidized bed is adjusted using a simple purge and make-up system of a type which will be readily familiar to those skilled in this art.

Suitably, the particles of the fluidized bed comprise any suitable inert fluidizable solid, for example coke.

In quenching the pyrolysis products of heavier hydrocarbon feedstocks which have a greater tendency to yield coke and tar by-products, it is preferred to use the process and apparatus described and illustrated with reference to FIG. 2, with the addition of cooling coils in the fluidized bed. In this case, the external treatment unit 11 is preferably used to burn away at least a portion of the accumulated coke on the particles and to cool the particles to a temperature which is equal to or less than that of the particles remaining in the fluidized bed. The heat may be recovered in any suitable form, for example as high-pressure steam or as preheat for reactants to the pyrolysis process.

In its application to quenching, the present invention enables the process operator to sharply define the end of the reaction which is to be quenched i.e. as being the point at which admixture of the reaction fluid and the solid particles takes place.

Preferably, the particulate solids forming the fluidized bed in this embodiment of the invention are any suitable inert fluidizable solid, for example coke. However, there are circumstances in which the use of chemically active solids may be appropriate. For example, in pyrolysing hydrocarbon feedstocks having a high content of sulphur and/or sulphur compounds, the use of solid particles with a high chemical affinity for sulphur compounds would enable these to be removed from the product gases and thereafter recovered in a separate operation, for example using the apparatus illustrated in FIG. 2 with a suitably designed external treatment unit 11.

In the hereinbefore described embodiments of the process and apparatus of this invention, the use of a single orifice for admitting reactant fluids to the fluidized bed has been described. In certain circumstances, process conditions may require the fluidized bed to handle fluid streams from more than one source. For example, it may be desired to treat, for example quench, the product gases from a process which is carried out in several similar reactors in parallel. If desired, therefore, the fluidized bed apparatus of this invention may be modified by expansion of the fluidized bed chamber to accommodate a plurality of fluid inlet means, each of said inlet means comprising an orifice which is located in support means for supporting the bed of fluidizable particles and which is narrow in comparison with the overall width of the bed. Preferably, the modified fluidized bed apparatus includes a plurality of second orifices, each located in a plate member or members within the apparatus, each of said second orifices being aligned substantially vertically above a corresponding orifice comprising the fluid inlet means for example as depicted in FIG. 3.

Conveniently, each second orifice is the bottom exit of an internal hopper filled by overflow from the fluidized bed. In embodiments where external treatment of solids from the fluidized bed is required, for example as described hereinbefore with reference to FIG. 2, it is convenient to remove the solids from the bed by a single conduit and then return them, after treatment, through a system of distributive conduits to each of the said internal hoppers. Alternatively, the solids may be treated in a number of external treatment units, each such unit serving one or more of said hoppers.

I claim:

1. Fluidized bed apparatus for mixing solid particles with a fluid comprising a chamber having a peripheral wall extending only in a vertical direction and an upwardly facing bottom wall for supporting a fluidized bed of particles and means for creating a fluidizing condition within the chamber, said means including a single, upwardly facing fluidizing orifice, said fluidizing orifice being centrally located in said bottom wall and means for injecting through said orifice a stream of fluid having a high angular velocity as it passes through said orifice, said orifice having a diameter less than the diameter of said bottom wall and less than 1/5 the inside diameter of said peripheral wall at the lower end thereof whereby the fluid entering the chamber forms a centrally located vortex into which the solid particles are drawn.

2. Fluidized bed apparatus for mixing solid particles with a fluid comprising: a chamber having a peripheral wall extending only in a vertical direction and an upwardly facing bottom wall for supporting a fluidized bed of particles; means for creating a fluidizing condition within the chamber including a single, upwardly facing fluidizing orifice, said fluidizing orifice being centrally located in said bottom wall; means for injecting through said orifice a stream of fluid having a high angular velocity as it passes through said orifice, said orifice having a diameter less than the diameter of said bottom wall and less than 1/5 the inside diameter of said peripheral wall at the lower end thereof whereby the fluid entering the chamber forms a centrally located vortex into which the solid particles are drawn; and means for introducing solid particles into the vortex, said introducing means comprising a hopper centrally located in said chamber above said fluidizing orifice so that there is an annular space between the hopper and the peripheral wall of said chamber, said hopper having a bottom exit in the form of an orifice located above and in substantial alignment with said fluidizing orifice, and said hopper having an open upper end within the chamber for receiving solid particles from the fluidized bed.

3. Fluidized bed apparatus for mixing solid particles with a fluid comprising: a chamber having a vertically extending peripheral wall and an upwardly facing bottom wall for supporting a fluidized bed of particles; means for creating a fluidizing condition within the chamber including a single, upwardly facing fluidizing orifice, said fluidizing orifice being centrally located in said bottom wall; means for injecting through said orifice a stream of fluid having a high angular velocity as it passes through said orifice, said orifice having a diameter less than the diameter of said bottom wall and less than 1/5 the inside diameter of said peripheral wall at the lower end thereof whereby the fluid entering the chamber forms a centrally located vortex into which the solid particles are drawn; means for removing a stream of solid particles from said chamber and means for introducing solid particles into the vortex, said introducing means comprising a hopper centrally located in said chamber above said fluidizing orifice so that there is an annular space between the hopper and the peripheral wall of said chamber, said hopper having a bottom exit in the form of an orifice located above and in substantial alignment with said fluidizing orifice, and conduit means for returning the removed stream of particles to the upper end of said hopper.

4. Apparatus for mixing a particulate solid and a fluid comprising a fluidized bed apparatus including a chamber having a vertically extending peripheral wall and an upwardly facing bottom wall for supporting a fluidized bed of particles; means for creating a fluidizing condition within the chamber, said means including a plurality of upwardly facing fluidizing orifices located in said bottom wall, means for injecting through each of said fluidizing orifices a stream of fluid having a high angular velocity as it passes through said fluidizing orifices, said fluidizing orifices each having a diameter less than 1/5 of the inside diameter of said peripheral wall at the lower end thereof, said apparatus further comprising second orifices located in one or more plate members within the apparatus, each of said second orifices being aligned substantially vertically above a respective fluidizing orifice; means for introducing solid particles to each of said second orifices, said means comprising solid particle supply conduits located in said apparatus above said plate member or said plate members, each of said supply conduits having a bottom exit connected to one of said plate members thereby forming for each supply conduit said second orifice.

* * * * *